United States Patent [19]

Vidueira

[11] Patent Number: 5,225,072
[45] Date of Patent: Jul. 6, 1993

[54] PROCESSES FOR THE SEPARATION OF AROMATIC HYDROCARBONS FROM A HYDROCARBON MIXTURE

[75] Inventor: Jose A. Vidueira, White Plains, N.Y.

[73] Assignee: UOP, Des Plaines, Ill.

[21] Appl. No.: 563,138

[22] Filed: Aug. 3, 1990

[51] Int. Cl.$^5$ .............................................. B01D 3/40
[52] U.S. Cl. ................................... 208/313; 208/321; 208/322; 208/333; 208/334
[58] Field of Search ............... 208/313, 321, 322, 333, 208/334

[56] References Cited

U.S. PATENT DOCUMENTS

| | | | |
|---|---|---|---|
| 3,492,222 | 11/1967 | Van Tassell | 208/321 |
| 3,551,327 | 3/1969 | Kelly et al. | 208/321 |
| 3,714,033 | 1/1973 | Somekh et al. | 208/321 |
| 3,864,244 | 2/1975 | Van Tassell | 208/321 |
| 3,864,245 | 2/1975 | Van Tassell | 208/321 |
| 3,966,589 | 6/1976 | Somekh | 208/321 |
| 4,058,454 | 11/1977 | Asselin | 208/321 |
| 4,081,355 | 3/1978 | Preusser et al. | 208/313 |
| 4,260,476 | 4/1981 | Vidueira et al. | 208/321 |
| 4,401,560 | 8/1983 | Vidueira et al. | 208/321 |
| 4,498,980 | 2/1985 | Forte | 208/321 |
| 4,586,986 | 5/1986 | Preusser et al. | 203/22 |
| 4,595,491 | 6/1986 | Berns | 208/326 |
| 4,664,783 | 5/1987 | Preusser et al. | 208/313 |
| 4,693,810 | 9/1987 | Forte et al. | 208/321 |
| 4,776,927 | 10/1988 | Emmrich et al. | 203/58 |

OTHER PUBLICATIONS

McCabe & Smith, Unit Operations of Chemical Engineering, McGraw Hill Book Company, Inc., 1956, pp. 586-587.
Kirk-Othmer Encyclopedia of Chemical Technology, 3rd. Ed., vol. 9, John Wiley & Sons, New York, 1980, pp. 672-679.
McKetta & Cunningham, Encyclopedia of Chemical Processing & Design, Marcel Dekker, Inc., New York, 1962, pp. 96-97.
Olsen et al, Unit Processes and Principles of Chemical Engineering, pp. 1-3.
Perry's Chemical Engineer's Handbook Sixth Edition McGraw-Hill Book Company, pp. 3-62.

Primary Examiner—Theodore Morris
Assistant Examiner—William C. Diemler
Attorney, Agent, or Firm—Thomas K. McBride; John G. Tolomei; Richard P. Silverman

[57] ABSTRACT

Processes are disclosed for the separation of aromatic hydrocarbons from feedstreams containing mixtures of aromatic and non-aromatic hydrocarbons using extractive distillation with an aromatic selective solvent in order to separate the aromatic hydrocarbons from the non-aromatic hydrocarbons. A rich solvent stream comprising the aromatic hydrocarbons and solvent is withdrawn from the extractive distillation column and passed to a steam stripping column to provide a regenerated lean solvent stream, a side-cut stream comprising the aromatic hydrocarbons and a stripper overhead stream comprising non-aromatic hydrocarbons which are passed as a reflux stream to the extractive distillation column. Various solvents are disclosed and an especially preferred solvent is sulfolane.

23 Claims, 2 Drawing Sheets

PROCESSES FOR THE SEPARATION OF AROMATIC HYDROCARBONS FROM A HYDROCARBON MIXTURE

FIELD OF THE INVENTION

The present invention relates generally to the separation of aromatic hydrocarbons from a hydrocarbon mixture, and more particularly to process employing extractive distillation and steam stripping to separate aromatic hydrocarbons from feedstreams containing mixtures of aromatic and non-aromatic hydrocarbons.

BACKGROUND OF THE INVENTION

One type of process for the recovery of high purity aromatic hydrocarbons such as benzene, toluene and xylenes (BTX) from various hydrocarbon feedstreams including catalytic reformate, hydrogenated pyrolysis gasoline, etc., utilizes an aromatic selective solvent to extract the aromatic hydrocarbons by liquid-liquid extraction as the primary separating step. Typically, in the practice of such processes, a hydrocarbon feed mixture is contacted in an extraction zone with an aromatic extraction solvent which selectively extracts the aromatic components from the hydrocarbon feedstock, thereby forming a raffinate phase comprising one or more non-aromatic hydrocarbons, and an extract phase comprising solvent having aromatic components dissolved therein.

The aromatic hydrocarbons are typically recovered from the extract phase, i.e., separated from the aromatic extraction solvent and further purified by one or more distillation steps. Often, extractive and/or steam distillation is employed to assist in recovering the aromatic hydrocarbons from the solvent because both methods are particularly effective as compared to other separation techniques such as simple distillation.

In many liquid-liquid extraction processes, the raffinate phase from the extraction zone is purified by water-washing. Typically, the water used for washing the raffinate phase is obtained from the aqueous phase of an overhead, or side-draw, distillate from an extract phase steam distillation column, i.e., condensed steam, in order to provide an efficient, integrated water circulation loop. The aqueous phase, which has low levels of solvent, is then passed to one or more raffinate wash columns where residual aromatic extraction solvent is recovered from the raffinate phase. Spent raffinate wash water is typically passed to a steam generator, or otherwise vaporized, along with any other solvent-containing water streams that may be present in the process to provide stripping steam which is introduced to the extract phase distillation columns as noted above.

One process for producing high purity aromatics is described in U.S. Pat. No. 3,714,033, issued to Somekh et al., and provides for the use of a liquid-liquid extraction column and a single distillation column wherein both extractive distillation and a steam stripping occur. The patent discloses the preferred use of a polyalkylene glycol solvent which can provide a high purity aromatics product.

Another process for producing high purity aromatics is described in U.S. Pat. No. 4,058,454, issued to Asselin, and provides for the use of a liquid-liquid extraction column and extractive and steam distillation in separate columns. A particularly suitable class of solvents for use in accordance with the above-identified patent is commonly referred to as the sulfolane type which can provide a high purity aromatic product.

Still another process for producing high purity aromatics is disclosed in U.S. Pat. No. 4,081,355, issued to Preusser et al., and describes a process for recovering highly pure aromatic substances from mixtures of hydrocarbons which contain, in addition to the aromatic substances, large amounts of non-aromatic substances by liquid-liquid extraction in combination with an after arranged extractive distillation whereby the liquid-liquid extraction of the starting hydrocarbon mixture is carried out to provide an extract, introducing this extract into an after arranged extractive distillation for further separating said extract whereby the sump product (extract phase) formed is drawn off and introduced into an after arranged distillation column where it is separated into an aromatic and a solvent fraction, while the head product of the extractive distillation (raffinate phase) is reintroduced into the bottom of the extractor for liquid-liquid extraction thereof, wherein there is used in both of the extracting stages, as selective solvent, morpholine and/or N-substituted morpholine in admixture with water.

In addition to the above-described liquid-liquid extraction process, some processes for separating aromatic hydrocarbons from mixtures with non-aromatic hydrocarbons have been proposed which use extractive distillation as the primary separating step. Generally, the extractive distillation processes provide higher recoveries of the heavier aromatic hydrocarbons such as $C_8$ aromatics and lower recoveries of light aromatics such as benzene than the liquid-liquid extraction processes.

Extractive distillation is a widespread practical and useful process for separating mixtures of materials and in particular of hydrocarbons, which cannot or can only partially be separated by simple distillation based on the boiling points of their components. In contrast to the liquid-liquid extraction frequently employed for separation of this nature, extractive distillation can exhibit advantages relating to apparatus construction and process engineering. For example, extractive distillation processes typically require only two distillation columns. Furthermore, in extractive distillation the mass transfer between the solvent and the material to be extracted can be improved due to the higher temperatures employed as compared to liquid-liquid extraction. This can result in an improved loading and for the same throughout and thus, smaller amounts of solvent can be sufficient. The obtainable advantages in apparatus construction can result in considerably smaller capital costs for an extractive distillation plant compared to those of a liquid-liquid extraction plant. The operating costs can also be lower and are sometimes only about 50% of those of a corresponding liquid-liquid extraction plant.

In liquid-liquid extraction the formation of two liquid phases is a precondition for successful separation of the starting materials. Ideally, one phase of the liquid-liquid extraction process consists of the solvent and of the components of the extract and the other phase consists of the components of the raffinate. It is frequently beneficial in liquid-liquid extraction to add water to the extraction for improving the selectivity and for favoring the formation of two liquid phases. Adding water results in the requirement of separate water circuits which can contribute to the increase of the capital costs of a liquid-liquid extraction plant but which cost is often far outweighed by the benefits of employing steam distillation for solvent recovery and purification of the aromatic product.

The underlying premise for the justification for employing extractive distillation has been completely different. The solvent employed in many extractive distillation processes is anhydrous in order to eliminate the requirement of separate water circuits. The separating effect in extractive distillation is based on the change of the vapor pressures of the individual components present in the mixture to be separated in the presence of the solvent. The changes are in the direction as to increase the vapor pressure difference between the components to be separated into either the extract or into the raffinate. Thus, the raffinate can be distilled off at the top of the extractive distillation column as the lower boiling fraction. Accordingly, it has been thought that aqueous systems were unnecessary and, therefore, undesirable.

The processes disclosed in the following patents are typical of the extraction distillation processes used for aromatic hydrocarbon recovery.

U.S. Pat. No. 4,586,986, issued to Preusser et al. discloses a method for recovering pure aromatic substances from a mixture of hydrocarbons containing both aromatic and non-aromatic fractions. The input mixture is fed through an extractive stage provided with a preliminary distillation column. In the preliminary stage the aromatics-containing product is treated at a pressure up to 20 bar and a temperature up to 300° C. The pressure is adjusted to a valve at which the operational temperature of the preliminary stage is higher than the pressure and temperature in the extractive stage and the heat of the vapors discharged from the preliminary stage is used for heating the extractive stage.

U.S. Pat. No. 4,664,783, issued to Preusser et al., discloses a method for the separation of aromatics from hydrocarbon mixtures, by means of extractive distillation, employing as selective solvent N-substituted morpholine, the substitutions of which display no more than 7 carbon atoms. The raffinate produced as top product of the extractive distillation is subjected to a second distillation, whereby the produced sump product with a solvent content between 20–75% by weight and a temperature between 20°–70° C., is led into a separation container and there separated into a heavy and a light phase. The heavy phase is then recycled into the extractive distillation column, whereas the light phase is recycled into the second distillation column.

U.S. Pat. No. 4,776,927, issued to Emmrich et al., discloses a process for the separation of aromatics from hydrocarbon mixtures through extractive distillation using N-substituted morpholine displaying substituents having no more than 7 carbon atoms as the selective solvent. Part of the solvent is delivered to the uppermost plate of the extractive distillation column and the remainder of the solvent, preferably amounting to between 10 and 40% by weight, is introduced into the extractive distillation column in at least two partial streams onto plates above the inlet for the hydrocarbon mixture. The temperature of the respective solvent partial streams is adjusted to neither exceed the temperature of the corresponding delivery plates nor fall below this temperature by more than 10° C.

U.S. Pat. No. 4,595,491, issued to Berns, discloses a process for the separation of an aromatic hydrocarbon from a hydrocarbon mixture of varying aromatic content, by means of extractive distillation, employing as a selective solvent, an N-substituted morpholine, wherein the N-substituent contains up to 7 carbon atoms. In the entry product, the weight ratio of light non-aromatic hydrocarbons to heavy non-aromatic hydrocarbon should amount to at least 0.4 to 1. The light non-aromatic hydrocarbon necessary for adjustment of this ratio can be either introduced directly into the lower part of the extractive distillation column, or added to the entry product before introducing the latter to the extractive distillation column.

In view of the two types of processes described above for separating aromatic hydrocarbons from mixtures with non-aromatic hydrocarbons, i.e., the liquid-liquid extraction processes and the extractive distillation processes, improved processes are sought which can combine the beneficial aspects of the two types of processes. More specifically, improved processes are sought which incorporate extractive distillation as the primary separation step in separating the aromatic hydrocarbons from the non-aromatic hydrocarbons and which also incorporates the steam distillation aspect of the liquid-liquid extraction processes for separating the aromatic hydrocarbons from the aromatic extraction solvents. In addition, further improvements are sought whereby the entire process can be performed in as few as two distillation columns, i.e., an extractive distillation column and a steam stripping column apart from miscellaneous equipment such as water-wash columns and the like. Furthermore, it is desired to utilize the aqueous phase condensate effluents from the extractive distillation column and the steam stripping column, for one or both of, providing stripping steam in the stripping column or for use as a raffinate wash water to recover aromatic extraction solvent from the raffinate.

SUMMARY OF THE INVENTION

In accordance with the present invention, there is now provided a process for recovering highly purified aromatic hydrocarbons from feedstreams containing aromatic and non-aromatic hydrocarbons by a combined distillation process using extractive distillation with an aromatic extraction solvent in a first distillation column followed by steam stripping of the extract from the extractive distillation column in a second distillation column to provide an aromatic product and a regenerated lean solvent stream which can be recycled back to the extractive distillation column. The process of the present invention includes the steps of (a) passing the feedstream to an extractive distillation column maintained at distillation conditions effective to separate aromatic from non-aromatic hydrocarbons and contacting the feedstream within said column with a lean solvent stream comprising an aromatic selective solvent and a reflux hydrocarbon stream comprising non-aromatic hydrocarbons; b) withdrawing a raffinate stream comprising non-aromatic hydrocarbons from an overhead section of said column; c) withdrawing a rich solvent stream comprising the aromatic selective solvent, aromatic hydrocarbons and non-aromatic hydrocarbons from a bottom section of said column; d) passing the rich solvent stream to a stripping column maintained at stripping conditions effective to separate the aromatic selective solvent from the aromatic hydrocarbons and contacting the rich solvent stream within the stripping column with stripping steam; e) withdrawing a stripper overhead stream comprising water and non-aromatic hydrocarbons from an overhead section of the stripping column; f) withdrawing a stripper bottoms stream comprising the lean solvent stream from a bottom section of said stripping column; and g) withdrawing a side-cut stream comprising aromatic hydrocarbons from an intermediate section of said stripping column.

In preferred aspects of the present invention, the process further includes heating and cooling steps such as: cooling the raffinate stream by indirect heat exchange with the feedstream thereby heating the feedstream prior to the passing it to the extractive distillation column; at least partially condensing the raffinate stream to provide a raffinate hydrocarbon phase and a raffinate aqueous phase; at least partially condensing the stripper overhead stream to provide an overhead hydrocarbon phase and an overhead aqueous phase; at least partially condensing the side-cut stream to provide a side-cut hydrocarbon phase comprising aromatic hydrocarbons and a side-cut aqueous phase; cooling the lean solvent stream by indirect heat exchange with a stripping water stream comprising at least a portion of at least one of the raffinate aqueous phase, the overhead aqueous phase; or the side-cut aqueous phase; and further cooling the cooled lean solvent stream by indirect heat exchange with the rich solvent stream. It is additionally preferred that the reflux hydrocarbon stream comprise the overhead hydrocarbon phase from the stripping column.

In another preferred aspect of the invention, the process further comprises the step of contacting the raffinate hydrocarbon phase with at least a portion of one of the overhead aqueous phase or the side-cut aqueous phase from the stripping column to provide a purified raffinate product having a reduced amount of extraction solvent and a spent wash water stream comprising aromatic selective solvent.

Essentially any solvent that is effective for performing the extractive distillation step in the extractive distillation column can be used as the aromatic selective solvent of the present invention. Preferred solvents include polyalkene glycols, such as tetraethylene glycol, either alone or mixed with glycol ethers, such as methoxytriglycol ether and sulfolane type solvents. The most preferred solvent for use in accordance with the present invention is sulfolane, which produced enhanced results, i.e., substantially lower energy consumption and higher throughput capacities (lower solvent to feed ratios) as compared to another suitable solvent (tetraethylene glycol).

DETAILED DESCRIPTION OF THE INVENTION

Figure 1:
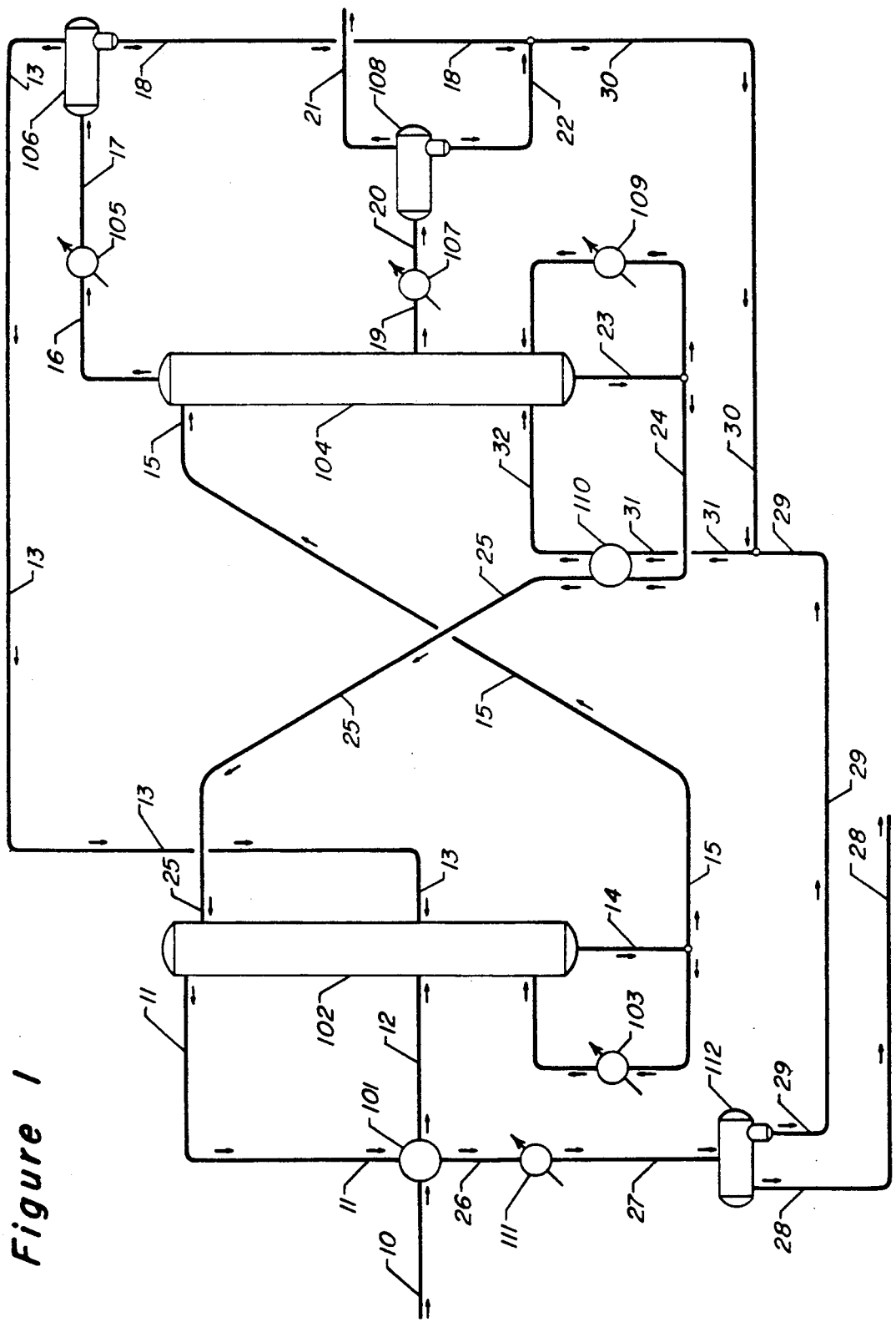
FIG. 1 illustrates a process flowscheme in accordance with the present invention wherein the solvent is sulfolane.

Hydrocarbon feedstreams suitable for utilization in the process of the present invention include many different aromatic-non-aromatic mixtures having a substantially high enough concentration of aromatic hydrocarbons to economically justify the recovery of the aromatic hydrocarbons as a separate product stream. Generally, the present invention is applicable to hydrocarbon feed mixtures containing from about 15-90% by weight non-aromatic hydrocarbons. Typical aromatic feedstreams suitable for use with the present invention will contain from about 55-90 vol. % non-aromatic hydrocarbons with non-aromatic hydrocarbon concentrations as high as 95% being suitable in some instances. A suitable carbon range for the hydrocarbon feedstream is from about 5 carbon atoms per molecule to about 20 carbon atoms per molecule, and preferably from 5 to 10 carbon atoms per molecule.

One suitable source of hydrocarbon feedstream is a depentanized fraction from the effluent from a conventional catalytic reforming process unit for the reforming of a naphtha feedstream. Another suitable source of feedstream is the liquid by-product from a pyrolysis gasoline unit which has been hydrotreated to saturate olefins and diolefins, thereby producing an aromatic hydrocarbon feedstream suitable for the separation technique described herein.

Still another suitable feedstream is a lube oil fraction such as a light distillate to heavy distillate, bright stock, etc., which have boiling points between about 400° and about 1200° F. The aromatic hydrocarbons present in heavy hydrocarbons feeds, e.g., lubricating oils, generally include: alkylbenzenes, indenes, tetralins, indenes, naphthalenes, fluorenes, acenaphthalenes, biphenyls, phenanltrenes, anthracenes, discenaphthalenes, pyrenes, chripenes, diaceanthrancenes, benzyprenes and other various aromatic feed components.

An especially preferred feedstream for use in the present invention is one recovered from a catalytic reforming unit, comprises single ring aromatic hydrocarbons of the $C_6$–$C_9$ range which are also mixed with corresponding boiling range paraffins and naphthenes which are present in the product from a catalytic reforming unit.

Solvent compositions which may be utilized in the practice of the present invention are those selected from the classes which have high selectivity for aromatic hydrocarbons. These aromatic selective solvents generally contain one or more organic compounds containing in their molecule at least one polar group, such as a hydroxyl, amino, cyano, carboxyl or nitro radical. In order to be effective, the organic compounds of the solvent composition having the polar radical should have a boiling point greater than the boiling point of water when water is included in the solvent composition for enhancing its selectivity. In general, the aromatic selective solvent should also have a boiling point greater than the end boiling point of the aromatic component to be extracted from the hydrocarbon feed mixture.

Organic compounds suitable for use as part of the solvent composition are preferably selected from the group of those organic-containing compounds which include the aliphatic and cyclic alcohols, cyclic monomeric sulfones, the glycols and glycol ethers, as well as the glycol esters and glycol ether esters. The mono- and polyalkylene glycols in which the alkylene group contains from 2 to 4 carbon atoms, such as ethylene glycol, diethylene glycol, triethylene glycol, and tetraethylene glycol, propylene glycol, dipropylene glycol, and tripropylene glycol, as well as the methyl, ethyl, propyl and butyl ethers of the glycol hydroxyl groups and the acetic acid esters thereof, constitute a satisfactory class of organic solvents useful in admixture with water as the solvent composition for use in the present invention.

Some of these solvents, when combined with other cosolvents, can provide mixed solvents having desirable properties and as such are useful as aromatic selective solvents of the present invention. One such mixed solvent comprises as one component the low molecular weight polyalkylene glycols of the formula:

$$HO-[CHR_1-(CHR_2R_3)_n-O]_m-H$$

wherein n is an integer from 1 to 5 and is preferably the integer of 1 or 2; m is an integer having a value of 1 or greater, preferably between about 2 to about 20 and most preferably between about 3 and about 8; and wherein $R_1$, $R_2$ and $R_3$ may be hydrogen, alkyl, aryl, aralkyl or alkylaryl and are preferably hydrogen and alkyl having between 1 and about 10 carbon atoms and most preferably are hydrogen. Examples of the polyalkylene glycol solvents employable herein are diethylene glycol, triethylene glycol, 1,3-butylene glycol, 1,2-butylene glycol, 1,5-pentaethylene glycol, and mixtures thereof and the like. Preferred solvents are diethylene glycol, triethylene glycol, tetraethylene glycol being most preferred. One such cosolvent component comprises a glycol ether of the formula:

$$R_4O-[CH_5-(CHR_6-)-_xO]_y-R_7$$

wherein $R_4$, $R_5$, $R_6$ and $R_7$ may be hydrogen alkyl, aryl, aralkyl, alkylaryl and mixtures thereof with the proviso that $R_4$ or $R_7$ are not both hydrogen. The value of x is an integer from 1 to 5, preferably 1 or 2 and y may be an integer from 1 to 10 and is preferably from 2 to 7, and most preferably from 2 to 5. $R_4$, $R_5$, $R_6$ and $R_7$ are preferably selected from the group consisting of hydrogen and alkyl having 1 to about 10 carbons with the proviso that $R_4$ and $R_7$ may not both be hydrogen and most preferably $R_4$ is alkyl having from 1 to 5 carbons and $R_5$, $R_6$ and $R_7$ are hydrogen. The mixture(s) of solvent and cosolvent is selected such that at least one solvent and one cosolvent are provided to form the mixed solvent. The cosolvent generally comprises between about 0.1 and about 99 percent of the mixed solvent, preferably between about 0.5 and about 80 percent and more preferably between about 5 and about 60 percent by weight based on the total weight of the mixed solvent. The above-described mixed solvents are fully disclosed in U.S. Pat. No. 4,498,980, hereby incorporated by reference.

Another typical aromatics selective solvent utilized in commercial aromatic extraction processes which is especially preferred for use in accordance with the practice of this invention, is commonly referred to as sulfolane (tetrahydrothiphene,1-1 dioxide) and has the following structural formula:

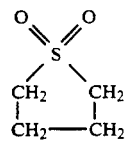

Also suitable are those sulfolane derivatives corresponding to the structural formula:

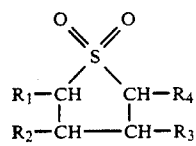

wherein $R_1$, $R_2$, $R_3$ and $R_4$ are independently selected from the group consisting of hydrogen, an alkyl radical containing from about 1 to about 10 carbon atoms, an aralkyl radical having from about 7 to about 12 carbon atoms, and an alkoxy radical having from about 1 to about 8 carbon atoms. Other solvents which may be included within this process are the sulfolenes, such as 2-sulfolene or 3-sulfolene which have the following structures:

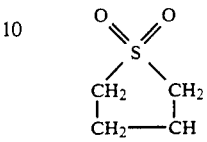

Other typical solvents which have a high selectivity for separating aromatics from non- aromatic hydrocarbons and which may be processed within the scope of the present invention are 2-methylsulfolane, 2,4-dimethylsulfolane, methyl-2-sulfonyl ether, N-aryl-3-sulfonylamine, 2-sulfonyl acetate, dimethylsulfoxide, N-methyl pyrrolidone, etc.

The aromatic selectivity of the solvent can usually be enhanced by the addition of water to the solvent. Preferably, the solvents utilized in the practice of this invention contain small quantities of water in order to increase the selectivity of the solvent for aromatic hydrocarbons without reducing substantially the solubility of the solvent for aromatic hydrocarbons. Accordingly, the solvent composition of the present invention preferably contains from about 0.1% to about 20% by weight water and, more preferably, about 0.5 to about 10% by weight depending upon the particular solvent utilized and the process conditions at which the extractive distillation column and the stripper column are operated.

Aromatic hydrocarbons contained in the foregoing feedstreams are separated from the non-aromatic hydrocarbons by contacting the feedstream in an extractive distillation column maintained under conditions effective to promote the separation of the aromatic hydrocarbons from the non-aromatic hydrocarbons. The precise conditions used in the distillation column can be determined by one skilled in the art, although it is generally preferred that the distillation conditions include a temperature of from about 200°–400° F. and a pressure of from about 15–100 psia.

The extractive distillation column will also contain a suitable number of trays or other packing material effective to perform the desired separation. The details of such trays and packing are known to those skilled in the art and accordingly do not need to be further discussed herein.

Preferably the feedstream is introduced to an intermediate section within the extractive distillation column. In the extractive distillation column, the feedstream is contacted with a lean solvent stream comprising an aromatic selective solvent which is preferably introduced into an upper section of the distillation column, and additionally contacted with a reflux hydrocarbon stream comprising non-aromatic hydrocarbons preferably obtained from the overhead hydrocarbon condensate from the stripping column as hereinafter described. The reflux hydrocarbon stream is preferably introduced to an intermediate section within the extractive distillation column. A raffinate stream comprising non-aromatic hydrocarbons is withdrawn from an overhead section of the distillation column. A rich solvent stream comprising the aromatic extraction solvent is withdrawn from a bottom section of the distillation column.

The rich solvent stream obtained from the extractive distillation column is then passed to the steam stripping column which is maintained under steam stripping conditions effective to separate the aromatic selective solvent from the aromatic hydrocarbons. The precise conditions used within the stripping column can be determined by those skilled in the art, but preferably the stripping conditions include a temperature of from about 150°–500° F. and a pressure of from about 1 to 100 psia.

As noted above with regard to the extractive distillation column, the steam stripping column also contains suitable trays or other packing material, the type of which is known to those skilled in the art and need not be discussed further herein.

The term "rich solvent", as used herein, denotes a mixture comprising an aromatic selective solvent of the present invention and aromatic hydrocarbons dissolved therein wherein the concentration of the aromatic hydrocarbons is increased relative to a regenerated or lean solvent. Similarly, the term "lean solvent", as used herein, denotes an aromatic selective solvent of the present invention that has been at least partially regenerated, i.e., has capacity for aromatic hydrocarbons and has a reduced concentration of aromatic hydrocarbons relative to the rich solvent.

In the steam stripping column, the rich solvent is contacted with steam in order to separate the solvent from the hydrocarbons and provide a stripper overhead stream which is withdrawn from an overhead section of the stripping column. The stripper overhead stream is preferably at least partially condensed to provide an overhead hydrocarbon phase and an overhead aqueous phase. As noted before, at least a portion of the overhead hydrocarbon phase is preferably recycled to the extractive distillation column as reflux. A side-cut stream comprising the aromatic hydrocarbons and water is withdrawn from an intermediate section of the stripping column, and in one aspect of the present invention, preferably partially condensed to provide a side-cut hydrocarbon phase comprising aromatic hydrocarbons and a side-cut aqueous phase. A stripper bottoms stream comprising lean solvent is withdrawn from a bottom section of the stripping column and at least a portion of it is passed to an upper section of the extractive distillation column as noted above.

Generally, to accomplish the separation in the extractive distillation column, the ratio of the extraction solvent to hydrocarbon feed is in the range from about 2 to about 20 parts by volume of extraction solvent to one part by volume of feed, the ratio from about 2:1 to about 10:1 being preferred and the ratio from about 2:1 to about 6:1 being the most preferred. The broad range for the ratio of the extraction solvent to hydrocarbon may be expanded upon depending on the particular solvent, the amount of water in the extraction solvent and the like. The optimum solvent to feed ratio also depends upon whether high recovery (yield) or high purity (quality) is desired although the instant process will allow for both high recovery and high purity.

Also embodied within the extractive distillation process of the present invention is the concept of refluxing the extractive distillation column with hydrocarbons, preferably by recycling the hydrocarbon portion of the overhead from the stripping column. By refluxing the heavy non-aromatics in the feedstream with light non-aromatics, the resulting non-aromatics are more readily separable from the aromatics. It is preferred that this reflux stream comprise relatively light non-aromatic hydrocarbons but significant quantities of aromatic hydrocarbons, i.e., 30–60% by weight, may be present in the reflux stream. The exact amount of reflux introduced into the extractive distillation column varies depending on the degree of non-aromatic hydrocarbon rejection desired in the extraction zone. Preferably, the reflux is at least 5% volume of the rich solvent phase, so as to insure effective refluxing of the heavy non-aromatic hydrocarbons. According to the process of the present invention it is preferred that at least a portion, if not all, of the light non-aromatic reflux required is provided by a non-aromatic fraction removed as an overhead from an upper section of the steam stripping column. This fraction is withdrawn as a vapor and contains water (steam) which is preferably condensed and removed before the non-aromatics are passed as reflux to the extractive distillation zone. In accordance with the present invention, the preferred reflux to feed ratio, i.e., reflux rate to feedstream rate, is in the range of from about 0.2:1 to about 1:1 and the more preferred reflux to feed ratio is in the range of from about 0.2:1 to about 0.7:1.

In a preferred aspect of the invention, instead of condensing the side-cut stream from the steam stripping column, the side-cut distillate is passed in vapor phase to a small column, e.g., about 10 or fewer trays, for rectification to provide a purified aromatic product. This rectification zone can be a separate column or an integral part of the steam distillation column.

In the operation of the rectification zone, the side draw distillate is passed to a lower section of the rectification zone to separate therein the aromatic hydrocarbons from the aromatic selective solvent. This separation is accomplished by maintaining the rectification zone under conditions including a temperature of about 100° F. to about 400° F. and a pressure of about 50 mm. Hg to about 25 psig, preferably 1 psig to about 15 psig, and withdrawing from an upper section of the rectification zone a vapor fraction relatively free of solvent comprising aromatic hydrocarbons and water (steam). This vapor fraction is condensed and the aromatics recovered are relatively free of non-aromatics and extraction solvent.

In one variation, the extract is removed as product and at least a portion of the aqueous phase of the condensate is returned to an upper section of the rectification zone as reflux. Any remaining portions of the aqueous phase which are essentially solvent free, are preferably used to wash the raffinate from the extractive distillation column. At least a portion, and preferably all, of the bottoms from the rectification zone which contain water and solvent are then passed to a lower section of the steam stripping column to provide stripping medium. It is to be noted that the rectifier bottoms can be heat-exchanged with other streams, e.g., the bottoms from the steam stripping column, to vaporize the stripping medium prior introducing it into the steam stripping column.

In another variation, the aqueous phase of the condensate is not used to reflux the rectification zone. Instead, at least a portion of the extract phase is returned to an upper section of the rectification zone as reflux. Any remaining portions are preferably removed as product. The aqueous phase is, preferably, used to wash the raffinate. At least a portion, and preferably all, of the bottoms product of the rectification zone is returned to an upper section of the steam stripping column, preferably at about the same location, e.g., one tray below the location from which the side draw is withdrawn.

The rectification technique described above can provide an aqueous phase that is essentially solvent free, i.e., low ppm levels. This aqueous phase can conveniently be used to wash the raffinate from the extractive distillation column in order to recover the solvent dissolved therein. Preferably, the spent raffinate wash water is used to provide at least a portion of the stripping medium used in the steam distillation column. At least a portion of the bottoms from the steam stripping column which comprises the lean solvent, is passed to the extractive distillation column as hereinbefore described.

Figure 2:
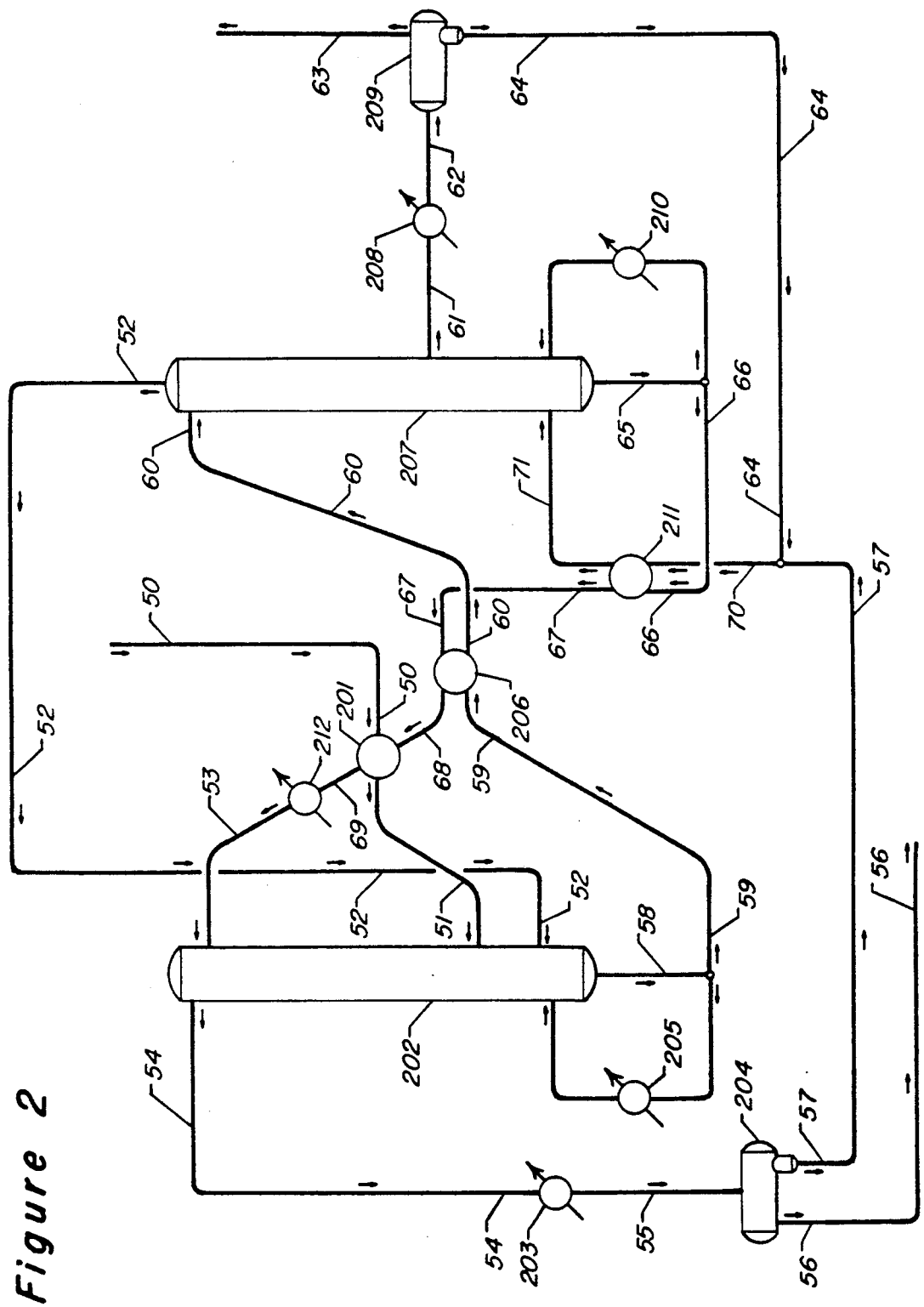
FIG. 2 illustrates a flowscheme in accordance with the present invention wherein the solvent is tetraethylene glycol.

The further description of the method of this invention is presented with reference to the attached schematics, FIG. 1 and FIG. 2. The Figures represent preferred aspects of the invention and are not intended to be a limitation on the generally broad scope of the invention as set forth in the claims. Of necessity, some miscellaneous appurtenances including valves, pumps, separators, heat exchangers, reboilers, etc., have been eliminated. Only those vessels and lines necessary for a complete and clear understanding of the process of the present invention are illustrated.

FIG. 1 illustrates a process flow diagram of an aspect of the present invention wherein sulfolane solvent is used as the solvent.

A $C_6$-$C_9$ cut of a depentanized reformate containing aromatic and non-aromatic hydrocarbons is passed by line 10 at a temperature of about 80° F. and 30 psia through heat exchanger 101 wherein it is heated by indirect heat exchange with a raffinate stream in line 11, the source of which is hereinafter defined, to a temperature of about 226° F. and is passed by line 12 to extractive distillation column 102. A reflux hydrocarbon stream containing non-aromatic hydrocarbons is also introduced to distillation column 102 by line 13, the source of which is hereinafter defined. A raffinate stream comprising non-aromatic hydrocarbons is withdrawn from an upper section of distillation column 102, at a temperature of about 282° F. and passed by line 11, as hereinbefore described, through heat exchanger 101 wherein it is cooled to a temperature of about 156° F. and is passed by line 26 to water cooler 111 where it is cooled to about 100° F. and passed by line 27 to separation vessel 112 wherein a raffinate hydrocarbon phase and raffinate aqueous phase are formed and the raffinate hydrocarbon phase is withdrawn by line 28. The extractive distillation column is maintained at an average pressure of about 25 psia. A rich solvent stream is withdrawn from a bottom section of distillation column 102 by a line 14 at a temperature of about 235° F. and a portion thereof is heated in reboiler 103 and returned to the distillation column.

The remaining portion of the rich solvent stream is passed by line 15 to an upper section of stripping column 104. An aqueous overhead stream is withdrawn from an upper section of stripping column 104 which comprises non-aromatic hydrocarbons and is passed by line 16 through water cooler 105 then passed by line 17 to separator 106 wherein the hydrocarbon and aqueous phases are separated. At least a portion of the hydrocarbon phase is used for refluxing the extractive distillation column, as noted before, and is passed thereto by line 13. The aqueous phase is withdrawn from separator vessel 106 by line 18. An aqueous side-cut stream comprising the aromatic hydrocarbons is withdrawn from an intermediate section of stripping column 104 by line 19, is passed through water cooler 107 and then passed by line 20 to separator 108 wherein the side-cut hydrocarbon phase comprising the aromatic hydrocarbon product is separated from the aqueous phase. At this point, the aromatic product can be further purified as required by conventional means. Alternately, the side-cut withdrawn from line 19 can be passed in vapor phase to a rectification zone as described in the specification. The steam stripping column is maintained at an average pressure of about 24 psia.

A lean solvent stream is withdrawn by line 23 from a bottom section of stripping column 104 at a temperature of about 350° and a portion thereof is passed through reboiler 109 to reboil the stripping column, and the remaining portion is passed by line 24 through heat exchanger 110 wherein it is cooled by indirect heat exchange with a stripping water stream, the source of which is hereinafter defined, to a temperature of about 288° F. and then it is introduced to an upper section of the extractive distillation column 102.

At least a portion of one of the aqueous phases from the side-cut or the stripping column overhead, i.e., lines 18 or 22, is used as raffinate wash water to recover solvent from the raffinate in line 28. The raffinate washing (not shown) can be performed by conventional methods and need not be discussed herein. A spent raffinate wash water stream comprising the extraction solvent can then be recovered from the raffinate water washing step and introduced, for example, into line 29. The aqueous streams, i.e., lines 29 and 30, are then combined and passed by line 31 as stripping water to heat exchanger 110 wherein the stripping water is heated to a temperature of about 246° F. and is at least partially vaporized and passed by line 32 into a lower section of stripping column 104. Make-up water can be added as required preferably as wash water feed for the raffinate wash.

FIG. 2 illustrates a process flow diagram in accordance with the present invention wherein tetraethylene glycol is used as the solvent.

A feedstream identical to that described with reference to FIG. 2 is passed by line 50 at a temperature of about 80° and pressure of about 30 psia through heat exchanger 201 where it is heated by indirect heat exchange with a lean solvent stream in line 68, the source of which is hereinafter defined, to a temperature of about 238° F. and is introduced to an intermediate section of extractive distillation column 202 which is maintained at an average pressure of about 19 psia. The feedstream is contacted in distillation column 202 with a reflux stream comprising non-aromatic hydrocarbons introduced into a lower section of the column by line 52, the source of which is hereinafter defined, and a lean solvent stream introduced into an upper section of the distillation column by line 53, the source of which is hereinafter defined. A raffinate stream is withdrawn at a temperature of about 142° F. by line 54 and is cooled in water cooler 203 to a temperature of about 100° F. and is passed by line 55 to separation vessel 204 wherein the raffinate hydrocarbon phase and raffinate aqueous phase are separated. The raffinate hydrocarbon phase is withdrawn by line 56 and is subjected to water washing as described with reference to FIG. 1. A rich solvent stream is withdrawn from a lower section of distillation column 202 by line 58 and a portion thereof is reboiled in reboiler 205 and introduced to the lower section of the distillation column.

The remaining portion of the rich solvent is passed by line 59 at a temperature of about 230° through heat exchanger 206 wherein it is heated by indirect heat exchange with a lean solvent stream in line 67, the source of which is hereinafter defined, to a temperature of about 277° F. and is passed by line 60 to stripping column 207. Stripping column 207 is maintained at an average pressure of about 28 psia. An aqueous stripper overhead comprising non-aromatic hydrocarbons is withdrawn from an upper section of stripping column 207 and is passed, without separation, by line 52 to extractive distillation column 202 as reflux. A side-cut stream is withdrawn from stripping column 207 at a temperature of about 279° F. and is passed by line 61 through water cooler 208 wherein it is cooled to about 130° F. and passed by line 62 to separator 209 wherein an aqueous phase and a hydrocarbon phase containing the aromatic product are formed. The hydrocarbon phase containing the aromatic product is withdrawn by line 63 and can be further purified as discussed with reference to FIG. 1. A lean solvent stream is withdrawn from a lower section of stripping column 207 at a temperature of about 343° F. and a portion thereof is passed to reboiler 210 and then to a lower section of the stripping column.

The remaining portion of the lean solvent is passed by line 66 through heat exchanger 211 wherein it is cooled by indirect heat exchange with a stripping water stream 70, the source of which is hereinafter defined, and is thereafter passed by line 67 through heat exchanger 206 wherein it is further cooled by indirect heat exchange with the rich solvent, as hereinbefore described, to a temperature of about 250° and is then passed by line 68 through heat exchanger 201 wherein it is further cooled to a temperature of about 199° F. by indirect heat exchange with the feedstream, as hereinbefore described. The lean solvent is then passed by line 69 to water cooler 212 wherein the lean solvent stream is cooled to a temperature of about 120° F. before being introduced into an upper section of the extractive distillation column by line 53.

As noted with reference to FIG. 1, a portion of one of the aqueous phases is preferably used as raffinate wash water to recover extraction solvent from the raffinate stream. The spent raffinate wash water along with the aqueous phase from lines 57 and 64 are combined to form a stripping water stream in line 70 which is passed to heat exchanger 211 wherein it is heated from a temperature of about 127° F. to a temperature of about 246° F. and at least partially vaporized before being introduced into a lower section of steam stripping column 207.

Table 1, below, sets forth the analysis of the feedstream described with reference to FIGS. 1 and 2. Table 2, below, illustrates the results of a computer simulation based on the two processes described with reference to FIGS. 1 and 2.

TABLE 1

| Feed Properties | |
|---|---|
| Component | Weight % |
| Benzene | 23.91 |
| Toluene | 17.61 |
| Xylenes | 3.43 |
| Pentanes | 201,100 |

TABLE 1-continued

| Feed Properties | |
|---|---|
| Component | Weight % |
| Hexanes | 35.67 |
| Heptanes | 12.11 |
| Octanes | 4.10 |
| Cyclopentane | 4.60 |
| Cyclohexane | 0.15 |
| Methyl-Cyclopentane | 0.79 |
| Methyl-Cyclohexane | 0.11 |
| | 100.00 |
| Flow rate | 201,100 lb/hr |

TABLE 2

| | Sulfolane Case FIG. 1 | Tetraethylene glycol Case FIG. 2 |
|---|---|---|
| Ratios | | |
| Solvent-to-feed (w/w) | 4.6 | 6.35 |
| Reflux-to-feed (w/w) | 0.18 | 0.39 |
| Feed Temperature, F. | 80 | 80 |
| Stripping water-to-aromatics (w/w) | 0.32 | 0.30 |
| Stripping water-to-solvent (w/w) | 0.033 | 0.021 |
| Water in Lean Solvent, Wt. % | 2.0 | 3.7 |
| Recovery | | |
| Benzene | 99.01 | 99.89 |
| Toluene | 99.88 | 100.0 |
| Xylenes | 100.0 | 100.0 |
| Impurity, ppmv | 1200 | 1200 |
| Extractive Distillation | | |
| Lean solvent temperature, F. | 288 | 120 |
| No. theoretical stages | 30 | 30 |
| Feed stage | 15 | 25 |
| Temperature, F. Top/Bottom | 282/235 | 142/230 |
| Pressure, psia Top/Bottom | 22.7/26.7 | 16.7/20.7 |
| Reboiler Duty, MM Btu/hr | 7.3 | 48.8 |
| Stripper Column | | |
| No. theoretical stages | 30 | 30 |
| Feed stage | 1 | 1 |
| Temperature, F. Top/Bottom | 227/350 | 272/343 |
| Pressure, psia Top/Bottom | 21.7/25.7 | 25.7/29.7 |
| Reboiler Duty, MM Btu/hr | 71.4 | 71.8 |
| Total Reboiler Duty, MM Btu/hr | 78.7 | 120.6 |
| Duty, Btu/lb aromatics | 870 | 1335 |

It can be seen from the results of the above-described example that both solvents simulated are suitable for use in accordance with the present invention. However, Table 2 illustrates that for recoveries and purities that were substantially the same, the energy consumption of the process from using the sulfolane solvent was surprisingly less than with the tetraethylene glycol solvent. More specifically, the duty reported as Btu's/lb of aromatics for the sulfolane case was only 65% of the duty for the tetraethylene glycol case, i.e., 870 Btu's/lb versus 1335 Btu's/lb. In addition, the solvent to feed ratio for the sulfolane case was only about 72% of the solvent to feed ratio required for the tetraethylene glycol case, i.e., 4.6 versus 6.5. The lower solvent to feed ratios are additionally beneficial because it can be translated to a higher throughput or capacity when operated at the higher solvent to feed ratio. Thus, for the same solvent circulation rate, the sulfolane solvent can process about 41% more feed based on the solvent to feed ratios from FIG. 2.

What is claimed is:

1. A process for separating aromatic hydrocarbons from a hydrocarbon feedstream containing aromatic and non-aromatic hydrocarbons, comprising;
   a) passing the feedstream which is at least partially vaporized to an extractive distillation column having a reboiler associated therewith maintained at extractive distillation conditions effective to separate aromatic from non-aromatic hydrocarbons and contacting the feedstream within said distillation column with a lean solvent stream comprising an aromatic selective solvent and a reflux hydrocarbon stream comprising non-aromatic hydrocarbons;

b) withdrawing a raffinate stream comprising non-aromatic hydrocarbons from an overhead section of said distillation column;

c) withdrawing a rich solvent stream comprising the aromatic selective solvent, aromatic hydrocarbons and non-aromatic hydrocarbons from a bottom section of said distillation column; and reboiling a portion of said rich solvent stream to provide a reboiled rich solvent and returning said reboiled rich solvent to said bottom section of said distillation column;

d) passing the rich solvent stream to a stripping column maintained at stripping conditions effective to separate the aromatic selective solvent from the aromatic hydrocarbons and contacting the rich solvent stream within said stripping column with stripping steam;

e) withdrawing a stripper overhead stream comprising water and non-aromatic hydrocarbons from an overhead section of said stripping column;

f) withdrawing a stripper bottoms stream comprising the lean solvent stream from a bottom section of said stripping column; and g) withdrawing a side-cut stream comprising aromatic hydrocarbons from an intermediate section of said stripping column.

2. the process of claim 1 wherein the aromatic selective solvent comprises a polyalkene glycol.

3. The process of claim 2 wherein the aromatic selective solvent comprises tetraethylene glycol.

4. The method of claim 1 wherein the aromatic selective solvent comprises a polyalkylene glycol of the formula:

$$HO-[CHR_1-(CH_2R_3)_n-O-]_mH$$

wherein n is an integer from 1 to 5, m is an integer having a value of 1 or greater and $R_1$, $R_2$ and $R_3$ may each be hydrogen, alkyl, aryl, aralkyl, alkylaryl and mixtures thereof and a glycol ether of the formula:

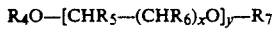

$$R_4O-[CHR_5-(CHR_6)_xO]_y-R_7$$

wherein $R_4$, $R_5$, $R_6$ and $R_7$ may each be hydrogen, alkyl, aryl, aralkyl, alkylaryl and mixtures thereof with the proviso that $R_4$ and $R_7$ are not both hydrogen; x is an integer from 1 to 5; and y may be an integer from 2 to 10.

5. The method of claim 4 wherein said aromatic selective solvent consists essentially of a polyalkylene glycol selected from the class consisting of diethylene glycol, triethylene glycol, tetraethylene glycol and mixtures thereof and a glycol either selected from the class consisting of methoxytriglycol, ethoxytriglycol, butoxytriglycol, methoxytetraglycol and ethoxytetraglycol and mixtures thereof wherein the glycol either comprises between about 0.1 and 99 percentage by weight of the solvent.

6. The process of claim 5 wherein the polyalkylene glycol is tetraethylene glycol and the glycol ether is methoxytriglycol.

7. The method of claim 1 wherein said aromatic selective solvent comprises a sulfolane type solvent.

8. The method of claim 1 wherein said aromatic selective solvent comprises sulfolane.

9. The process of claim 1 wherein the extractive distillation conditions include a temperature of from about 200° to 400° F. and a pressure of from about 15 to 100 psia.

10. The process of claim 1 wherein the stripping conditions include a temperature of from about 150° to 500° F. and a pressure of from about 1 to 100 psia.

11. The process of claim 1 further comprising cooling the raffinate stream by indirect heat exchange with the feedstream, thereby at least partially vaporizing the feedstream prior to passing it to said distillation column.

12. The process of claim 11 comprising at least partially condensing the raffinate stream to provide a raffinate hydrocarbon phase and a raffinate aqueous phase.

13. The process of claim 12 further comprising at least partially condensing the stripper overhead stream to provide an overhead hydrocarbon phase and an overhead aqueous phase.

14. The process of claim 13 wherein the reflux hydrocarbon stream comprises the overhead hydrocarbon phase.

15. The process of claim 14 comprising at least partially condensing the side-cut stream to provide a side-cut hydrocarbon phase comprising aromatic hydrocarbons and a side-cut aqueous phase.

16. The process of claim 15 further comprising cooling the lean solvent stream to obtain a cooled lean solvent stream by indirect heat exchange with a stripping water stream comprising at least a portion of at least one of the raffinate aqueous phase, the overhead aqueous phase or the side-cut aqueous phase.

17. The process of claim 16 wherein the stripping stream comprises at least a portion of the stripping water stream.

18. The process of claim 16 comprising further cooling the cooled lean solvent stream by indirect heat exchange with the rich solvent stream.

19. The process of claim 17 further comprising contacting the raffinate hydrocarbon phase with at least a portion of at least one of the overhead aqueous phase or the side-cut aqueous phase to provide a purified raffinate product and a spent wash water stream comprising aromatic selective solvent.

20. The process of claim 18 wherein the stripping stream further comprises at least a portion of the spent wash water stream.

21. The process of claim 15 further comprising purifying the side-cut hydrocarbon phase to provide a purified extract product rich in aromatic hydrocarbons.

22. The process of claim 1 wherein the feedstream includes aromatic hydrocarbons comprising at least one of benzene, toluene and xylenes.

23. The process of claim 1 wherein the feedstream includes non-aromatic hydrocarbons comprising paraffinic and cyclic hydrocarbons in the $C_5$–$C_8$ carbon range.

* * * * *